United States Patent [19]

Abbruzzese et al.

[11] Patent Number: 6,077,828
[45] Date of Patent: *Jun. 20, 2000

[54] METHOD FOR THE PREVENTION AND TREATMENT OF CACHEXIA AND ANOREXIA

[75] Inventors: Bonnie Chandler Abbruzzese, Dublin; Mark Anthony McCamish; Frederick Oliver Cope, both of Worthington; Stephen Joseph Demichele, Dublin, all of Ohio

[73] Assignee: Abbott Laboratories, Abbott Park, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/842,454

[22] Filed: Apr. 24, 1997

Related U.S. Application Data

[63] Continuation-in-part of application No. 08/635,179, Apr. 25, 1996, abandoned.

[51] Int. Cl.$^7$ .............................. A23J 3/16; A61K 38/17
[52] U.S. Cl. ......................... 514/21; 514/578; 514/725; 514/730; 514/739; 424/523; 426/72; 426/601; 426/602; 426/656; 426/800; 426/801
[58] Field of Search ........................... 424/523; 514/578, 514/725, 730, 739, 21; 426/72, 601, 602, 656, 800, 801

[56] References Cited

U.S. PATENT DOCUMENTS

| | | | |
|---|---|---|---|
| 4,615,839 | 10/1986 | Seto | 424/523 |
| 5,223,285 | 6/1993 | DeMichele et al. | 424/72 |
| 5,308,832 | 5/1994 | Garleb et al. | 514/2 |
| 5,330,972 | 7/1994 | Cope | 514/2 |
| 5,385,740 | 1/1995 | Tisdale et al. | 424/573 |
| 5,393,784 | 2/1995 | Richardson | 514/561 |
| 5,431,925 | 7/1995 | Ohmori et al. | 424/646 |
| 5,444,054 | 8/1995 | Garleb et al. | 514/54 |
| 5,457,130 | 10/1995 | Tisdale | 514/560 |

FOREIGN PATENT DOCUMENTS

| | | |
|---|---|---|
| 0367724 | 5/1990 | European Pat. Off. . |
| 0462398 | 12/1991 | European Pat. Off. . |
| 0756827 | 2/1996 | European Pat. Off. . |
| WO 9508349 | 3/1995 | WIPO . |
| WO 97 13415 | 4/1997 | WIPO . |

OTHER PUBLICATIONS

Utesjev et al. "immunomodulating and antioxidant effect of beta–carotene andessentiale in disturbed lipid metabolism" CA 129:184101, 1998.
Cho et al. "Lipid peroxidation and antioxidant status is affected fy different vitamin E levels when feeding fish oil" CA 120:132920, 1994.
Abstract of DE 3901048 Derwent 90–225190 (1990).
Keller, Ulrich, Pathophysiology of cancer cachexia, Supportive Care in Cancer (1993) 1:209–294.
Derwent –90–225190 (1990).
Derwent –Abstract 010905121 (1996).
Ottery, Faith D., M.D. Cancer Cachexia, Cancer Practice, Mar./Apr. 1994, vol. 2, No.2., pp. 123–131.
Ottery, Faith D., M.D., Supportive Nutrition to Prevent Cachexia and Improve Quality of Life, Seminars in Oncology, vol. 22, No. 2, Supplement 3 (Apr.), 1995, pp. 98–111/
Kern, Kenneth, M.D., et al., Cancer Cachexia, Journal of Parental and Enteral Nutrition, vol. 12, No. 3, pp. 286–294 (1988).
Heber, David, M.D., Ph.D., et al., Hormonal and Metabolic Abornalities in the Malnourished Cancer Patient; Effects on Host–Tumor Interaction, Journal of Parenteral and Enteral Nutirition, vol. 16, No. 6, Supplement, pp. 60S–64S (1992).
McNamara, Michael J., M.D., et al. Cytokines and Their Role in the Pathophysiology of Cancer Cachexia, Journal of Parenteral and Enteral Nutrition, vol. 16, No. 6, Supplement, pp. 50S–55S (1992).
Tisdale, M.J., Cancer Cachexia, Anti Cancer Drugs, vol. 4, pp. 113–125 (1993).
Bozzetti, Federico, M.D., Effects of Artificial Nutrition on the Nutritional Status of Cancer Patients, Journal of Parenteral and Enteral Nutrition, vol. 13, No. 4 pp. 406–420 (1989).
Derwent –011043748 (1996).
Derwent –011043746 (1996).
Derwent –008405601 (1990).
Todorov, Penio, et al., Characterization of a cancer cachectic factor, Nature, vol. 379, Feb. 22, 1996, pp. 739–742.
Wigmore, Stephen, et al., The Effect of Polyunsaturated Fatty Acids on the Progress of Cachexia in Patients with Pancreatic Cancer, Nutrition, vol. 12, No. 1, 1996, pp. S27–S30.
Tisdale, Michael J., et al., Inhibition of Lipolysis and Muscle Protein Degradation by EPA in Cancer Cachexia, Nutrition, vol. 12, 1996, pp. S31–S33.
Henderson, Robin A., et al., Effect of Fish Oil on the Fatty Acid Composition of Human Milk and Maternal and Infant Erythrcytes, Lipids, vol. 27, No. 11 (1992), pp. 863–869.
Tisdale, Michael J., et al., Inhibition of Weight Loss by ω–3 Fatty Acids in an Experimental Cachexia Model, Cancer Research 50, 5022–5026, Aug. 15, 1990.

(List continued on next page.)

*Primary Examiner*—Ceila Chang
*Attorney, Agent, or Firm*—J. Michael Dixon; Thomas D. Brainard

[57] ABSTRACT

The present invention relates to methods and nutritional compositions for the prevention and treatment of cachexia and anorexia. The methods of the invention comprise administering a composition comprising effective amounts of ω-3 fatty acids such as alpha-linolenic acid, stearidonic acid, eicosapentaenoic acid, docosapentaenoic acid, docosahexaenoic acid or mixtures thereof; of branched-chain amino acids valine, leucine, isoleucine or mixtures thereof; with or without reduced levels of tryptophan and 5-hydroxytryptophan; and of antioxidant system selected from the group comprising beta-carotene, vitamin C, vitamin E, selenium, or mixtures thereof.

20 Claims, No Drawings

OTHER PUBLICATIONS

Dinarello, Charles A., et al., Interleukin–1, Anorexia, and Dietary Fatty Acids, Annals of The New York Academy of Sciences, vol. 587, pp. 332–338 (1990).

Build Bulk and Muscle for that Competitive Edge, Herbalife Advertisement, Los Angeles, California, 90080–00210, 1996.

Cangiano, C., et al., Plasma and CSF Tryptophan in Cancer Anorexia, J Neural Transm (GenSect) 1990, 81:225–233.

Rossi–Fanelli, F., M.D., et al., Increased Availability of Tryptophan in Brain as Common Pathogenic Mechanism for Anorexia Associated with Different Diseases, Nutrition, vol. 7 No. 5, Sep./Oct. 1991.

Rossi–Fanelli, Filippo, et al., Plasma Tryptophan and Anorexia in Human Cancer, Eur J Cancer Clin Oncol, vol. 22, No. 1 pp. 89–95, 1986.

Krause, Rudolf, et al., Brain Tryptophan and the Neoplastic Anorexia–Cachexia Syndrome, Cancer, Sep. 1979, 44: pp. 1003–1008.

Meguid, Michael, et al., The Early Cancer Anorexia Paradigm: Changes in Plasma Free Tryptophan and Feeding Indexes, Journal of Parenteral and Enteral Nutrition, vol. 16, No. 6, Supplement, pp. 56S–59S (1992).

Anticancer Research, vol. 14, 1994, pp. 1451–1455, XP002035801, C. Cangiano, et al., "Cytokines, Tryptophan and Anorexia in Cancer Patients Before and After Surgical Tumor Ablation".

METHOD FOR THE PREVENTION AND TREATMENT OF CACHEXIA AND ANOREXIA

This application is a continuation-in-part of prior application Ser. No. 08/635,179 filed Apr. 25, 1996, now abandoned which is hereby incorporated by reference.

The present invention relates to methods and nutritional compositions for the prevention and treatment of cancer cachexia and anorexia. In the practice of the present invention patients are enterally administered ω-3 fatty acids including, but not limited to alpha-linolenic (18:3 ω-3), stearidonic (18:4 ω-3), eicosapentaenoic (20:5 ω-3), docosapentaenoic (22:5 ω-3), and docosahexaenoic (22:6 ω-3), in combination with antioxidants including, but not limited to, beta-carotene, vitamin C, vitamin E, selenium, or mixtures thereof; a source of amino-nitrogen with high levels of branched-chain amino acids including valine, leucine, isoleucine, and with or without reduced levels of tryptophan and 5-hydroxytryptophan.

BACKGROUND

Cancer cachexia is a syndrome characterized by anorexia, weight loss, premature satiety, asthenia, loss of lean body mass, and multiple organ dysfunction. The majority of patients with cancer whose disease progresses to metastatic disease develop cachexia during their treatment program and the cachexia contributes to their deaths. The frequency of weight loss in cancer patients ranges from 40% for patients with breast cancer, acute myelocytic leukemia, and sarcoma to more than 80% in patients with carcinoma of the pancreas and stomach. About 60% of patients with carcinomas of the lung, colon or prostate have experienced weight loss prior to beginning chemotherapy. Although the relationship between pretreatment malnutrition (weight loss) and adverse outcome is established, no consistent relationship has been demonstrated between the development of cachexia and tumor size, disease stage, and type or duration of the malignancy. Development of cachexia in the cancer patient is not caused simply by increased energy expenditure by the host or by the tumor. The malignant cachexia is partially related to reduced caloric intake.

Cancer cachexia is not simply a local effect of the tumor. Alterations in protein, fat, and carbohydrate metabolism occur commonly. For example, abnormalities in carbohydrate metabolism include increased rates of total glucose turnover, increased hepatic gluconeogenesis, glucose intolerance and elevated glucose levels. Increased lipolysis, increased free fatty acid and glycerol turnover, hyperlipidemia, and reduced lipoprotein lipase activity are frequently noted. The weight loss associated with cancer cachexia is caused not only by a reduction in body fat stores but also by a reduction in total body protein mass, with extensive skeletal muscle wasting. Increased protein turnover and poorly regulated amino acid oxidation may also be important. Presence of host-derived factors produced in response to the cancer have been implicated as causative agents of cachexia, e.g., tumor necrosis factor-α (TNF) or cachectin, interleukin-1 (IL-1), IL-6, gamma-interferon (IFN), and prostaglandins (PGs) (e.g., $PGE_2$).

Anorexia, with progressive depletion of body stores leading to the cachectic state, is observed in 50% of cancer-bearing patients. Different mechanisms proposed to explain the pathogenesis of anorexia include: (i) increased production of cytokines such as TNF and IL-1, and (ii) increased serotoninergic activity within the central nervous system secondary to enhanced availability to the brain of its precursor, tryptophan. Dickerson, J. W. T. et al., 1976, *J. Neurochem* 27: 1245–1247 have suggested that diets should be selected to keep the ratio of plasma tryptophan to the sum of neutral amino acids constant. Cangiano, C., et al., 1994, *Anticancer Res.* 14: 1451–1456 has also disclosed that a close relationship between plasma free tryptophan concentration and anorexia in cancer patients supports the serotoninergic system activity in the pathogenesis of cancer anorexia.

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant metastatic sites. Clinical data and molecular biologic studies indicate that cancer is a multi-step process that begins with minor preneoplastic changes, which may under certain conditions progress to neoplasia causing metabolic effects such as cachexia.

Tumor cells differ from normal cells in their metabolism of fat in that tumor cells consume short-chain and medium-chain fatty acids poorly. For example, tumor-bearing mice fed a diet rich in medium-chain triglycerides had less weight loss with a marked reduction in tumor size compared with animals fed long-chain triglycerides. Moreover, there have been problems reported with the use of high levels of medium-chain triglycerides and use of structured lipids has been suggested in some total parenteral nutrition formulas. Moreover, these structured lipids do not provide the same benefits if administered enterally. U.S. Pat. Nos. 4,906,664 and 5,081,105 disclose the use of certain structured lipids in the treatment of cancer. Preparations for enteral nourishment including varying ratios of ω-6 to ω-3 (2.1:1–3.0:1) have also been used in oncologic patients. However, these preparations used proportionately larger amounts of ω-6 to ω-3 fatty acids. Furthermore, these preparations did not include additional amounts of branched-chain amino acids and antioxidants as set forth in the present invention. The use of the polyunsaturated fatty acid eicosapentaenoic acid is suggested for the treatment of cachexia by inhibiting lipolytic activity of lipolytic agents in body fluids and the activity of the enzyme guanidino-benzoatase. See Tisdale, M. J., and Beck, A., U.S. Pat. No. 5,457,130, issued Oct. 10, 1995; and Tisdale, et al. *Cancer Research* 50: 5022–5026 (August 1990). However, the product taught by Tisdale was in a solid dosage form, requiring an already ill patient to swallow 12–16 capsules per day. This method had serious drawbacks, including difficulty in swallowing, belching, and bad odor.

Thus, the prevention and/or treatment of cachexia and anorexia remain a frustrating problem. Both animal and human studies suggest that nutritional support is largely ineffective in repleting lean body mass in the cancer-bearing host. Randomized trials exploring the usefulness of total parenteral nutrition (TPN) support as an adjunct to cytotoxic antineoplastic therapy have demonstrated little improvement in treatment results. See for example Brennan, M. F., and Burt, M. E., 1981, *Cancer Treatment Reports* 65 (Suppl. 5): 67–68. This, along with a clear demonstration that TPN can stimulate tumor growth in animals suggests the routine use of TPN in cancer treatment is not justified. Kisner, D. L., 1981, *Cancer Treatment Reports* 65 (Suppl. 5): 1–2.

Long chain fatty acid bio-pathways and physiological actions are discussed in U.S. Pat. No. 5,223,285 to DeMichele, et al., the entirely of which is incorporated herein by reference.

Also of interest is U.S. Pat. No. 5,444,054 to Garleb, et al. and a related U.S. Pat. No. 5,780,451 (allowed application Ser. No. 08/221,349). These documents describe compositions and methods useful in the treatment of ulcerative colitis. Such compositions include a protein source that can be intact or hydrolyzed proteins of high biological value (col. 21); an indigestible oligosaccharide such as fructooligosaccharide; and a lipid blend containing a relatively high proportion of eicosapentaneoic acid, which contributes to a relatively high ω-3 to ω-6 fatty acid ratio.

SUMMARY OF THE INVENTION

The methods of the invention generally comprise inhibiting metabolic and cytokine associated features of cachexia in an individual by administering a nutritional composition comprising an effective amount of ω-3 fatty acids including, but not limited to alpha-linolenic acid, stearidonic acid, eicosapentaenoic acid, docosapentaenoic acid and docosahexaenoic acid, alone or in combination with each other. The invention also relates to administering a nutritional composition comprising effective amounts of branched-chain amino acids, valine, leucine, isoleucine, or mixtures thereof, and with or without a reduced amount of tryptophan and hydroxytryptophan. The invention further provides a method of reducing oxidative damage and anti-cancer drug-induced immunosuppression in a cancer patient by administering a nutritional composition comprising effective amounts of antioxidants including, but not limited to beta-carotene, vitamin C, vitamin E, selenium, or mixtures thereof.

In one aspect, the invention provides a method of preventing the onset of cachexia and/or anorexia, or treating existing cachexia and/or anorexia in a human comprising enterally administering to the human at least:

(a) an oil blend containing ω-6 fatty acids and at least 450 mg of ω-3 fatty acids, the weight ratio of ω-6 fatty acids to ω-3 fatty acids being from about 0.1 to about 3.0; and (b) a source of amino-nitrogen wherein 15% to 50% by weight of the amino acids of said source of amino-nitrogen are branched-chain amino acids; and (c) an antioxidant component comprised of at least one nutrient selected from the group comprising beta-carotene, vitamin C, vitamin E, selenium, or mixtures thereof.

These components may be administered in a single composition or in separate vehicles. Preferably, about 15% to about 25% of the amino-nitrogen is provided by branched-chain amino acids; most preferably, about 20%. It is also preferred that the source of amino nitrogen provides tryptophan in an amount of less than about 5.0% by weight of the total amount of the amino acids of said source of amino-nitrogen; more preferably at a level of less than 3% by weight.

In another aspect, the invention provides a method of preventing the onset of anorexia or of treating existing anorexia in a human comprising administering to the human a nutritional composition comprising amino-nitrogen wherein about 5 to 25 grams of branched-chain amino acids selected from valine, leucine, isoleucine, or mixtures thereof are present in an amount from about 15% to about 50% by weight, preferably about 15–25%, of the total amount of amino-nitrogen present in said nutritional composition, and wherein tryptophan in an amount not greater than about 5.0% by weight of the total amount of amino acids is present in said composition and wherein ω-6 and ω-3 fatty acids are present at a weight ratio of from about 0.1 to about 3.0 and at least one antioxidant is present in the nutritional composition.

There is further disclosed a method for preventing immunosuppression in a human comprising administering to the human a liquid nutritional composition comprising:

(a) an oil blend containing ω-6 and ω-3 fatty acids, the weight ratio ω-6 fatty acids to ω-3 fatty acids being about from 0.1 to about 3.0; and (b) an antioxidant component comprising about 2,500 to about 6,500 micrograms per liter beta-carotene, about 250 to about 1,000 milligrams per liter vitamin C, about 100 to about 500 I.U. per liter vitamin E, and about 75 to about 125 mcg per liter selenium.

There is also disclosed a method of enhancing the transport and efficacy of anticancer drugs in a human having a cancerous condition comprising administering to the human a nutritional composition comprising an oil blend containing ω-6 and ω-3 fatty acids, the weight ratio of total ω-6 fatty acids to ω-3 fatty acids being from about 0.1 to about 3.0.

In another aspect, the invention provides a liquid nutritional composition comprising per liter:

(a) at least 0.45 gm (450 mg) of ω-3 fatty acids and wherein the weight ratio of ω-6 fatty acids to ω-3 fatty acids is from about 0.1 to about 3.0;

(b) at least 50 grams of a source of amino-nitrogen wherein 15 to 50% by weight of the amino-nitrogen is branched-chain amino acids and wherein tryptophan is present in an amount less than about 5.0% by weight of the total amino-nitrogen; and (c) at least 1 gram of an antioxidant system comprising beta-carotene, vitamin C, vitamin E and selenium.

Generally, such compositions provide much higher levels of the ω-3 fatty acids: preferably from about 1.0 gm to about 100 gm per liter; more preferably, from about 5.0 gm to about 10 gm per liter. Similarly, it is preferred that about 15–25% (typically about 20%) by weight of the source of amino-nitrogen is branched-chain amino acids.

The various methods according to the present invention may be accomplished by feeding a single composition that contains all the components of the invention (ω-6 to ω-3 oil, branched-chain amino acids and antioxidant system) or each component may be fed individually. Further, these methods may be accomplished through the consumption of pills or capsules that contain the elements of the claimed invention. In one embodiment of the invention, a nutritional liquid formulation containing all the elements of the invention is contemplated except for the branched-chain amino acids which may be consumed in the form of a pill or tablet.

In yet another co-embodiment of the invention, a liquid nutritional product contains all the elements of the composition, wherein the branched-chain amino acids are dispersed within the liquid in the form of microcapsules. This administration of the branched-chain amino acids in the form of capsules, tablets, pills and/or microcapsules is advantageous since the organoleptic or taste properties of the amino acids are very objectionable.

In contrast to the prior art, the nutritional composition of the present invention is not restricted to correcting metabolism of just one nutrient class at a time, such as lipids or amino acids. Instead, a preferred nutritional multinutrient composition comprises a balanced formulation containing ω-3 fatty acids, antioxidants, branched-chain amino acids, and with or without a reduced level of tryptophan and 5-hydroxytryptophan. Such a composition can demonstrate strong inhibition of cachexia and anorexia associated with a variety of different cancers (disease states).

In yet another embodiment, the methods further optionally comprise administering the nutritional composition in combination with cancer chemotherapeutic agents, including but not limited to, 5-fluorouracil, mitomycin-C, adriamycin, chloroethyl nitrosoureas and methotrexate, to improve the transport of the drug into the target cancer cells and ultimately the efficacy of the anticancer agent.

The Examples presented below exemplify the use according to the methods of the invention of ω-3 fatty acids, antioxidants, branched-chain amino acids with or without a reduced level of tryptophan in nutritional therapy of cachexia and anorexia in human patients suffering from different cancers, including, but not limited to, liver, breast, lung, prostate, gastrointestinal and pancreatic cancer.

DETAILED DESCRIPTION OF THE INVENTION

"Cachexia" refers to a state of general ill health and malnutrition. It is often associated with and induced by malignant cancer, and is characterized by loss of appetite, loss of body mass, especially lean body mass, and muscle wasting.

"Anorexia" refers simply to a loss of appetite, whether brought on by medical or psychological factors. Anorexia is often closely associated with, and generally contributes to, the cachexia seen in patients with advanced cancers.

"Fatty acids" refer to a family of carboxylic acids having a hydrocarbon chain, generally from about 12 to 24 carbons long. When unsaturated (having a double bond) at least one point in the hydrocarbon chain, such fatty acids are designated by the position of the first double bond. ω-3 fatty acids have a first double bond at the third carbon from the methyl end of the chain; and include, but are not limited to, α-linolenic acid, stearidonic acid, eicosapentaenoic acid ("EPA"), docosapentaenoic acid and docosahexaenoic acid ("DHA") and the like. ω-6 fatty acids have a first double bond at the sixth carbon from the methyl end of the chain; and include, but are not limited to, linoleic acid, γ-linolenic acid, arachidonic acid ("AA"), and the like. The ratio of ω-6 fatty acids to ω-3 fatty acids is simply the ratio of the total amounts (usually expressed as weight) of each type.

Branched-chain amino acids are amino acids that have a fork or branch in the side chain. These include primarily those having a carbon-carbon branch, i.e. valine, leucine and isoleucine; but may also include other types of branches.

"Nutritional matrix" as used herein refers to a delivery vehicle that contains fats, amino nitrogen and carbohydrates and provides some or all of the nutritional support for a patient in the recommended daily amounts. Frequently a nutritional matrix will contain vitamins, minerals, trace minerals and the like to provide balanced nutrition.

"Cytokines" as used herein refer to the causative agents of cachexia in the cancer patient, produced by the individual in response to the presence of cancer, and include, but are not limited to, tumor necrosis factor (TNF) or cachectin, interleukin-1 (IL-1), IL-6 and gamma-interferon (IFN). TNF is produced by the macrophages in response to nonspecific stimuli including cancer, infection, trauma and stress. The mechanism of action in cancer cachexia involves an immune response to the tumor with the production of cytokines, which not only mediate tumor lysis but also the metabolic changes seen in cancer cachexia through specific TNF receptors and/or via the induction of other cytokine receptors.

While not intending the invention to be limited to any particular theory of operation, applicants describe below a probable mechanism. A mode of action of cytokines is mediated via interactions with receptors on the plasma membrane. This is typically defined as a "signal transduction event." In general, a cytokine receptor consists of an extracellular domain, a transmembrane region spanning the phospholipid bilayer of the plasma membrane, and an intracellular domain having either enzymatic activity or binding other molecules, so that a signal is delivered inside the cell in response to the cytokine ligand interaction. The signal transduction mechanisms involve second messengers, including phospholipases, adenylate cyclase and cyclic AMP, inositol phosphates, diacylglycerols and protein kinase C. More particularly, phospholipase A2 generates arachidonic acid, a precursor of dienoic prostaglandins, thromboxanes, prostacyclin and leukotrienes of the 4 series.

Cytokines such as TNF and IL-1 stimulate production of arachidonic acid metabolites which are important to their inflammatory and tissue damaging actions and are responsible for immunosuppression in general, and in exacerbating some paraneoplastic conditions including metabolic changes seen in cancer cachexia.

The invention is based, in part, on a method of inhibiting signal transduction and cytokine activity using nutritional compositions comprising high levels of ω-3 fatty acids, in particular, of the long chain (e.g. 20 or more carbons) ω-3 fatty acids, eicosapentaenoic (EPA) and docosahexaenoic (DHA).

Since administration of EPA and DHA results in a reduction of arachidonic acid in membrane phospholipids, such an effect not only diminishes the supply of arachidonic acid as a precursor for the dienoic eicosanoids but also inhibits their production through competitive inhibition by EPA. The cyclooxygenase and lipoxygenase metabolites of EPA have attenuated activity. Furthermore, ω-3 fatty acids, alpha-linolenic and stearidonic can be converted through elongation/desaturation to EPA; and similarly, DHA can be retroconverted to EPA. Thus, the methods of invention comprise methods of inhibiting cytokine activity (e.g., TNF, IL-1) and cancer cachexia by interfering with signal transduction at the receptor level and inhibiting arachidonic acid metabolism.

Incorporation of ω-3 fatty acids in membrane phospholipids not only alters the activity of membrane-associated enzymes (e.g., phospholipase A2) but also alters the balance between constituent saturated and unsaturated fatty acids and regulation of membrane fluidity, facilitates the transport of anticancer drugs into the cancer cells and thus enhances the efficacy of the drugs. Alberts, A. W., et al., 1978, *Biochim. Biophys. Acta* 509:239–250. In addition, the inhibition of arachidonic acid metabolism results in prevention and/or reversal of immunosuppression by reducing the production of prostaglandins and leukotrienes (PGE2 and LTB4), which are immunosuppressive.

The invention also provides a method of reducing the concentration of brain tryptophan and serotonin to prevent or inhibit premature satiety and cancer cachexia and/or anorexia in a cancer patient in whom the prevention and treatment of cancer anorexia is desired by administering effective amounts of branched-chain amino acids, valine, leucine, isoleucine, or mixtures thereof, and with or without a reduced amount of tryptophan.

The methods and compositions of the invention provide a method of manipulating the concentration of brain tryptophan by: (i) increasing the branched-chain amino acids, which provide competition for tryptophan for penetration across the blood-brain barrier; and (ii) reduced levels of tryptophan and 5-hydroxytryptophan in relation to branched-chain amino acids in the nutritional composition of the invention. Such an intervention can increase appetite and thus prevent and/or treat cancer anorexia.

The methods and compositions of the invention also provide a method of reducing the risk or progression of certain symptoms of cancer, such as cancer cachexia and anorexia by administering antioxidant nutrients including, but not limited to, beta-carotene, vitamin C, vitamin E, selenium, or mixtures thereof. Epidemiological evidence indicates that a combination of beta-carotene, vitamin E and selenium can effect a reduction in cancer risk in some populations. Blot, N. J. et al., 1993, *J. Natl. Cancer Inst.* 85: 1483–1492. Furthermore, vitamin E is added to satisfy any additional requirements as a result of a higher intake of ω-3 polyunsaturated fatty acids. By the administration of the antioxidant nutrients of the invention to cancer patients having cachexia and whose immune system has been depressed on account of chemotherapy and/or oxidative burden, improvements in the nutritional status, as well as prevention and treatment of immunosuppression and cachexia can be achieved.

Nutritional support in the cancer patient can be categorized as (i) supportive, in which nutrition support is instituted to prevent nutrition deterioration in the adequately nourished patient or to rehabilitate the depleted patient before definitive therapy; (ii) adjunctive, in which nutrition support plays an integral role in the therapeutic plan; and (iii) definitive, in which aggressive nutrition support is required for the patient's existence. The routes for providing nutrition support include an oral diet, tube feeding and peripheral or total parenteral nutrition. The preferred embodiment for nutritional methods and compositions of the invention is by the oral route.

An alternate to oral feeding is tube feeding by means of nasogastric, nasoduodenal, esophagostomy, gastrostomy, or jejunostomy tubes.

A typical nutritional composition useful in the method of this invention will have a caloric distribution as follows: about 12 to 24% (target 21%) from a source of amino-nitrogen, about 40 to 65% (target 61%) from carbohydrate and about 10 to 35% (target 18%) from fat. More particularly, the oil blend may comprise approximately 30% of ω-3 fatty acids, preferably largely consisting of eicosapentaenoic acid and docosahexaenoic acid. Dietary oils used in the preparation of the nutritional composition generally contain ω-3 fatty acids in the triglyceride form and include, but are not limited to canola, medium chain triglycerides, fish, soybean, soy lecithin, corn, safflower, sunflower, high-oleic sunflower, high-oleic safflower, olive, borage, black currant, evening primrose and flaxseed oil. Table 1 sets forth both preferred amounts and ranges for an oil blend useful in the invention. Specifically, the weight ratio of ω-6 fatty acids to ω-3 fatty acids in the lipid blend according to the invention is about 0.1 to 3.0. The daily delivery of ω-3 fatty acids should be at least 450 mg and may vary depending on body weight, sex, age and medical condition of the individual. As mentioned, higher levels are desired for adult human consumption: for example, from about 0.5 to 50 gm daily, more preferably from about 2.5 to 5 gm daily.

TABLE 1

OIL BLEND
(% total weight of lipid blend)

| OIL | PREFERRED | RANGE |
|---|---|---|
| Canola | 9.3% | 5.0–40.0% |
| MCT | 16.2% | 10.0–50.0% |
| Fish | 65.0% | 25.0–80.0% |
| Soybean | 5.5% | 3.0–30.0% |
| Soy lecithin | 4.0% | 2.0–6.0% |

Table 2 presents the fatty acid profile of an exemplary oil blend useful in the present invention. The weight ratio of the total ω-6 fatty acids to the total ω-3 fatty acids in this embodiment is 0.26 to 1 which is within the claimed range for this invention.

TABLE 2

FATTY ACID PROFILE
(% of total fatty acids by weight)

| OIL | % |
|---|---|
| Caproic (6:0) | 0.53 |
| Caprylic (8:0) | 10.35 |
| Capric (10:0) | 7.16 |
| Lauric (12:0) | 0.29 |
| Myristic (14:0) | 3.53 |
| Palmitic (16:0) | 7.41 |
| Palmitoleic (16:1ω7) | 5.73 |
| Stearic (18:0) | 1.39 |
| Oleic (18:1ω9) | 15.23 |
| Linoleic (18:2ω6) | 7.21 |
| Gamma-linoleic (18:3ω6) | 0.21 |
| Alpha-linoleic (18:3ω3) | 2.21 |
| Stearidonic (18:4ω3) | 2.40 |
| Arachidic (20:0) | 0.13 |
| Eicosenoic (20:1ω9) | 0.74 |
| Arachidonic (20:4ω6) | 0.87 |
| Eicosapentaenoic (20:5ω3) | 17.14 |
| Erucic (22:1ω9) | 0.17 |
| Docosapentaenoic (22:5ω3) | 2.08 |
| Docosahexaenoic (22:6ω3) | 7.73 |
| Nervonic (24:1ω9) | 0.14 |
| Others | 7.35 |
| Total | 100.00 |

TABLE 3:

LIPID BLEND CHARACTERISTICS

| % ω-3 fatty acids | 30.51 |
|---|---|
| % ω-6 fatty acids | 9.67 |
| % ω-9 fatty acids | 15.28 |
| % saturated fatty acids | 27.07 |
| % monounsaturated fatty acids | 19.33 |
| % polyunsaturated fatty acids | 40.17 |
| ω-6/ω-3 ratio | 0.32 |
| 18:2ω6/18:3ω3 ratio | 4.26 |
| 18:3ω3, % total energy | 0.33 |
| 18:2ω6, % total energy | 1.41 |
| 18:1ω9, % total energy | 2.42 |
| PUFAs, % total calories | 7.23 |
| saturated fatty acids, % total calories | 4.87 |
| EPA (20:5ω3) per 8 oz container, g | 1.09 |
| DHA (22:6ω3) per 8 oz container, g | 0.46 |

Table 3 (above) sets forth selected characteristics of an oil blend useful in the method of this invention. However, it will be realized that the characteristics may vary among other formulas useful for this invention, depending on the specific oils added and the ratios in which they are used.

An amino acid profile for a nutritional composition useful in the invention is presented in Table 4.

TABLE 4

AMINO ACID PROFILE

| Amino Acid | g/100 g Protein |
|---|---|
| Aspartic Acid | 7.08 |
| Threonine | 4.34 |
| Serine | 5.68 |
| Glutamic Acid | 20.58 |
| Proline | 10.55 |
| Glycine | 1.81 |
| Alanine | 3.04 |
| Valine | 5.90 |
| Methionine | 2.78 |
| Isoleucine | 4.77 |
| Leucine | 9.08 |
| Tyrosine | 4.79 |
| Phenylalanine | 4.96 |
| Histidine | 2.67 |
| Lysine | 7.27 |
| Arginine | 3.15 |
| Tryptophan | 0.99 |
| Cystine | 0.56 |
| Total BCAA | 19.75 |

The total amount of branched-chain amino acids ("BCAA") useful in the present invention is about 15–50 g/100 g protein (i.e. percent), preferably about 15–25 g/100 g. Thus, an 8 oz container of the nutritional composition would contain up to about 8g BCAAs per 16 grams of total protein. The daily delivery of BCAAs is about 5–26 g. In order to deliver such a high amount of the BCMs, and because the BCMs impart an unpleasant taste, the nutritional composition may be accompanied by 1–3 gelatin capsules containing BCAAs to provide the additional amount required above the inherent amount present in the liquid product. The preferred BCAAs are, but are not limited to, leucine, isoleucine and valine, and are predominantly bitter in taste. Therefore, administering the additional BCAAs in encapsulated form avoids taste problems which are encountered with the use of quantities greater than 20 g/100 g protein of BCAAs in the liquid product. The microencapsulated BCAAs may also be mixed with taste masking compounds including, but not limited to, polyphosphates, cyclodextrin (a cyclic glucose oligomer) and Thaumatin (a proteinaceous intense sweetener).

A representative antioxidant profile useful in the method of the invention is presented in Table 5 with range values and a preferred embodiment.

TABLE 5

ANTIOXIDANT PROFILE

| Antioxidant | Preferred | Range |
|---|---|---|
| Beta-carotene | 5,000 µg/L | 2,500–6,500 µg/L |
| Vitamin E | 300 IU/L | 100–500 IU/L |
| Vitamin C | 650 mg/L | 250–1,000 mg/L |
| Selenium | 90 µg/L | 78.8–125 µg/L |

The overall nutrient profile of this example is set forth in Table 6. In a specific embodiment of this invention, the nutritional product provides at least 100% of the U.S. RDA for vitamins and minerals in 1184 mL (five 8 fluid ounce servings), which would provide 1184 kcal per day.

If used as a sole source of nutrition, and assuming a 2000 kcal diet, between 8 and 9 servings (237 mL; 8 fluid ounces) of this illustrative formulation would be required. However, as seen from example IV below, there is benefit derived from supplementation with as few as two servings per day. Thus a minimum daily amount of long chain $\omega$-3 fatty acids is preferably about 3 grams, calculated as (1.06 g EPA+0.46 g DHA) times 2 8 oz servings. Of course, if more servings are consumed to provide additional calories, more $\omega$-3 fatty acids will be administered, up to a practical maximum of about 14 grams per day (about 9 servings at same fatty acid levels). Levels of the fatty acids, antioxidants and/or source of amino nitrogen on a per liter basis are not crucial, except to the extent that a reasonable volume of fluid should supply the recommended daily amounts consistent with the invention. Determination of a reasonable volume is easily within the ambit of those skilled in the art, especially in view of the specific guidance found in the examples.

TABLE 6

NUTRIENT PROFILE

| Nutrient | Qty/Liter |
|---|---|
| Protein, g | 67.40 |
| Fat, g | 27.20 |
| Carbohydrate, g | 207.00 |
| Total Dietary Fiber, g | 10.70 |
| Indigestible Oligosaccharide (FOS), g | 12.40 |
| Gum Arabic, g | 9.10 |
| Soy Polysaccharide, g | 1.60 |
| Beta-carotene, µg | 5000 |
| Vitamin A, IU | 5500 |
| Vitamin D, IU | 800.00 |
| *Vitamin E, IU | 300.00 |
| Vitamin K, µg | 135.00 |
| Vitamin C, mg | 650.00 |
| Folic Acid µg | 1900 |
| Thiamine, mg | 6.50 |
| Riboflavin, mg | 5.00 |
| Vitamin $B_6$, mg | 5.00 |
| Vitamin $B_{12}$, µg | 18.00 |
| Niacin, mg | 40.00 |
| Choline, mg | 525.00 |
| Biotin, µg | 750.00 |
| Pantothenic Acid, mg | 24.00 |
| Sodium, mg | 1500 |
| Potassium, mg | 2000 |
| Chloride, mg | 1519 |
| Calcium, mg | 1800 |
| Phosphorous, mg | 1250 |
| Magnesium, mg | 450.00 |
| Iodine, µg | 175.00 |
| Copper, mg | 2.61 |
| Zinc, mg | 29.20 |
| Iron, mg | 22.20 |
| Selenium, µg | 90.00 |
| Chromium, µg | 125.00 |
| Molybdenum, µg | 206.00 |
| Carnitine, mg | 150.00 |
| Taurine, mg | 275.00 |
| Kcal/mL | 1 |

*d-alpha-tocopherol (all natural form) or dl-alpha-tocopherol acetate, or a combination of the two.

The following specific examples are set forth to illustrate various preferred embodiments of the invention but the scope of the invention is defined by the appended claims.

EXAMPLE I

The specific list of materials for manufacturing the nutritional cancer product of this Example I is presented in Table 7. Of course, various changes in specific ingredients and quantities may be made without departing from the scope of the invention.

TABLE 7

LIST OF MATERIALS

| INGREDIENT | AMOUNT |
|---|---|
| WATER | 31,605.21 kg |
| GUM ARABIC | 437.84 kg |
| ULTRATRACE/TRACE MINERAL PREMIX | 14.50 kg |
| ZINC SULFATE | 2969.89 gm |
| FERROUS SULFATE | 2856.50 gm |
| MANGANESE SULFATE | 784.60 gm |
| CUPRIC SULFATE | 423.11 gm |
| SODIUM MOLYBDATE | 21.39 gm |
| CHROMIUM CHLORIDE | 20.80 gm |
| SODIUM SELENITE | 8.11 gm |
| CITRIC ACID | 894.94 gm |
| SUCROSE (Carrier) | 6520.67 gm |
| POTASSIUM CITRATE | 50.00 kg |
| SODIUM CITRATE | 95.00 kg |
| POTASSIUM IODIDE | 9.00 gm |
| POTASSIUM CHLORIDE | 91.00 kg |
| CORN SYRUP SOLIDS | 5630.96 kg |
| MALTODEXTRIN | 1407.52 kg |
| MAGNESIUM PHOSPHATE DIBASIC | 131.00 kg |
| CALCIUM PHOSPHATE TRIBASIC (PREFERABLY MICRONIZED) | 47.50 kg |
| CALCIUM CARBONATE | 122.50 kg |
| SUGAR (SUCROSE) | 852.77 kg |
| FRUCTOOLIGOSACCHARIDE | 509.96 kg |
| MEDIUM CHAIN TRIGLYCERIDES (FRACTIONATED COCONUT OIL) | 172.69 kg |
| CANOLA OIL | 99.13 kg |
| SOY OIL | 58.63 kg |
| 57% VITAMIN A PALMITATE | 250.00 gm |
| 2.5% VITAMIN D | 35.00 gm |
| D-ALPHA-TOCOPHEROL ACETATE (R,R,R) | 10.65 kg |
| PHYLLOQUINONE | 6.50 gm |
| 30% BETA-CAROTENE | 824.00 gm |
| SOY LECITHIN | 42.64 kg |
| SODIUM CASEINATE | 1427.04 kg |
| PARTIALLY HYDROLYZED SODIUM CASEINATE | 1427.04 kg |
| SOY POLYSACCHARIDE | 85.28 kg |
| 75% WHEY PROTEIN CONCENTRATE | 184.46 kg |
| REFINED DEODORIZED SARDINE OIL | 692.87 kg |
| ASCORBIC ACID | 37.08 kg |
| 45% POTASSIUM HYDROXIDE | 25.96 kg |
| TAURINE | 12.00 kg |
| WATER SOLUBLE VITAMIN PREMIX | 4.50 kg |
| NIACINAMIDE | 1688.60 gm |
| CALCIUM PANTOTHENATE | 1092.24 gm |
| THIAMINE CHLORIDE HYDROCHLORIDE | 278.78 gm |
| PYRIDOXINE HYDROCHLORIDE | 268.34 gm |
| RIBOFLAVIN | 217.87 gm |
| FOLIC ACID | 37.82 gm |
| BIOTIN | 32.87 gm |
| CYANOCOBALAMIN | 0.75 gm |
| DEXTROSE (Carrier) | 882.74 gm |
| FOLIC ACID | 43.50 gm |
| CHOLINE CHLORIDE | 25.00 kg |
| L-CARNITINE | 7.00 kg |
| ARTIFICIAL STRAWBERRY FLAVOR | 31.75 kg |
| ARTIFICIAL CREAM FLAVOR | 18.14 kg |
| FD & C Red Dye No. 3 | 1,220.16 gm |

The liquid nutritional product of the present invention was manufactured by preparing three slurries which are blended together, combined with refined deodorized sardine oil, heat treated, standardized, packaged and sterilized. The process for manufacturing 45,360 kg (100,000 pounds) of the liquid nutritional product, using the List of Materials from Table 7, is described in detail below.

A carbohydrate/mineral slurry is prepared by first heating about 6,260 kg of water to a temperature in the range of about 71° C. to 77° C. with agitation. The gum arabic is then added to the water using a mixing apparatus. Next the ultratrace/trace mineral premix is added to the water and dissolved by agitating the resultant solution for at least one minute. The following minerals are then added, in the order listed, with high agitation: potassium citrate, sodium citrate, potassium iodide and potassium chloride. The corn syrup solids (Grain Processing Corporation, Muscatine, Iowa, U.S.A. under the trade designation "Maltrin M-200") and maltodextrin (Grain Processing Corporation, trade designation "Maltrin M-100") are then added to the slurry and the temperature of the slurry is maintained at about 71° C. with high agitation for at least about 20 minutes.

Add magnesium phosphate dibasic, calcium phosphate tribasic, and calcium carbonate to the slurry. Sugar (sucrose), and fructooligosaccharide (Golden Technologies Company, Golden, Colo., U.S.A. under the trade designation "Nutriflora-P- Fructo-oligosaccharide Powder (96%)") are added to the slurry. The completed carbohydrate/mineral slurry is held with high agitation at a temperature in the range of about 60–66° C. for not longer than 12 hours until it is blended with the other slurries.

An oil slurry is prepared by combining and heating the medium chain triglycerides (fractionated coconut oil), canola oil and soy oil to a temperature in the range of about 32–43° C. with agitation. The 57% vitamin A palmitate, 2.5% vitamin $D_3$, D-alpha-tocopherol acetate (R,R,R form; Distillation Products Industries, a division of Eastman Kodak Chemical Company, Rochester, N.Y. U.S.A. under the trade designation "Eastman Vitamin E 6-81 D-Alpha Tocopherol Acetate Concentrate"), phylloquinone and 30% beta-carotene are added to the slurry with agitation. The soy lecithin is then added to the slurry with agitation. The completed oil slurry is held under moderate agitation at a temperature in the range of about 32–43° C. for not longer than 12 hours until it is blended with the other slurries.

A protein-and-fiber-in-water slurry is prepared by first heating about 19,678 kg of water to a temperature in the range of about 60–63° C. with agitation. Sodium caseinate, partially hydrolyzed sodium caseinate (distributed by New Zealand Milk Products, Santa Rosa, Calif., U.S.A. under the trade name Alanate 167) and soy polysaccharide are blended into the slurry using a mixing apparatus. The temperature of the slurry is lowered to about 57–60° C. and then the 75% whey protein concentrate is added to the slurry using a mixing apparatus. The completed protein-and-fiber-in-water slurry is held under agitation at a temperature in the range of about 54–60° C. for not longer than 2 hours before being blended with the other slurries.

The oil slurry and the protein-and-fiber-in-water slurry are blended together with agitation and the resultant blended slurry is maintained at a temperature in the range of about 54–66° C. After waiting for at least one minute the carbohydrate/mineral slurry is added to the blended slurry from the preceding step with agitation and the resultant blended slurry is maintained at a temperature in the range of about 54–66° C. The vessel which contained the carbohydrate/mineral slurry should be rinsed with about 220 kg of water and the rinse water should be added to the blended slurry. The refined deodorized sardine oil (distributed by Mochida International Company, Limited, Shinjuku-ku, Tokyo, Japan under the trade designation "50% Omega-3 marine oil EPA:DHA 28:12 with 0.8% mixed tocopherol as antioxidant") is then added to the slurry with agitation. (In a most preferred method of manufacture the sardine oil would be slowly metered into the product as the blend passes through a conduit at a constant rate.) Preferably after at least 5 minutes the pH of the blended slurry is determined. If the pH of the blended slurry is below 6.55, it is adjusted with dilute potassium hydroxide to a pH of 6.55 to 6.8.

After waiting a period of not less than one minute nor greater than two 45 hours the blended slurry is subjected to deaeration, Ultra-High-Temperature (UHT) treatment, and homogenization, as described below:

A. Use a positive pump for supplying the blended slurry for this procedure.
B. Heat the blended slurry to a temperature in the range of about 66–71° C.
C. Deaerate the blended slurry to 25.4–38.1 cm of Hg.
D. Emulsify the blended slurry at 61–75 Atmospheres.
E. Heat the blended slurry to a temperature in the range of about 120–122° C. by passing it through a plate/coil heat exchanger with a hold time of approximately 10 seconds.
F. UHT heat the blended slurry to a temperature in the range of about 144–147° C. with a hold time of approximately 5 seconds.
G. Reduce the temperature of the blended slurry to be in the range of about 120–122° C. by passing it through a flash cooler.
H. Reduce the temperature of the blended slurry to be in the range of about 71–82° C. by passing it through a plate/coil heat exchanger.
I. Homogenize the blended slurry at about 265 to 266 Atmospheres.
J. Pass the blended slurry through a hold tube for at least 16 seconds at a temperature in the range of about 74–85° C.
K. Cool the blended slurry to a temperature in the range of about 1–70° C. by passing it through a large heat exchanger.

Store the blended slurry at a temperature in the range of about 1–7° C., preferably with agitation.

Preferably at this time appropriate analytical testing for quality control is conducted. Based on the test results an appropriate amount of dilution water (10–38° C.) is added to the blended slurry with agitation.

A vitamin solution, a flavor and a color solution are prepared separately and then added to the blended slurry.

The vitamin solution is prepared by heating about 394 kg of water to a temperature in the range of about 43–66° C. with agitation, and thereafter adding the following ingredients, in the order listed: Ascorbic Acid, 45% Potassium Hydroxide, Taurine, Water Soluble Vitamin Premix, Folic Acid, Choline Chloride, and L-Carnitine. The vitamin solution is then added to the blended slurry with agitation.

The flavor solution is prepared by adding the artificial strawberry flavor and artificial cream flavor to about 794 kg of water with agitation. A nutritional product according to the present invention has been manufactured using an artificial strawberry flavor distributed by Firmenich Inc., Princeton, N.J., U.S.A. under the trade designation "Art. strawberry 57.883/A" and an artificial cream flavor distributed by Firmenich Inc. under the trade designation "Art Cream 59.200/A". The flavor solution is then added to the blended slurry with agitation.

A color solution is prepared by adding the FD&C Red Dye No. 3 to about 121 kg of water with agitation. The color solution is then added to the blended slurry with agitation.

If necessary, diluted potassium hydroxide is added to the blended slurry such that the product will have a pH in the range of 6.4 to 7.0 after sterilization. The completed product is then placed in suitable containers and subjected to sterilization. Of course, if desired aseptic processing could be employed.

The product made according to the procedure of this example contains the oil blend of Table 8, below, the the fatty acid properties of Tables 2 and 3, and the amino acid profile of Table 4, all set forth above.

TABLE 8

| OIL BLEND (% total weight of lipid blend) | |
|---|---|
| OIL | Percent Total Lipids |
| Canola | 9.3% |
| MCT | 16.2% |
| Fish | 65.0% |
| Soybean | 5.5% |
| Soy lecithin | 4.0% |

EXAMPLE II

The objective of this experiment was to evaluate the organoleptic characteristics of nutritional composition of the invention fortified by the addition of branched-chain amino acids incorporated at two different levels. To measure organoleptic properties, three taste standards, described in Table 9, were prepared to rank the bitter and sour intensity of the test compositions containing branched-chain amino acids.

TABLE 9:

| TASTE INTENSITY SCALE | | | | |
|---|---|---|---|---|
| Standard | Basic Taste | Intensity | Concentration* by Weight | Representative Products |
| 1 | Sour | 1 | 0.05% Citric Acid | Milk Chocolate, Coffee Whole Peanuts |
| 2 | Bitter | 1 | 0.05% Caffeine | Milk Chocolate |
| 3 | Bitter | 2 | 0.10% Caffeine | Beer |

*Aqueous solutions

Two test compositions (designated "high" and "low") were prepared by adding selected branched-chain amino acids ("BCAA") to the liquid nutritional composition of Example I. A control composition of Example I that did not contain the supplemental branched-chain amino acids was also evaluated for flavor characteristics. The specific amino acids and amounts added are given in Table 10. In both test compositions the branched-chain amino acids did not completely disperse in the nutritional composition due to their hydrophobic nature, and small clumps of branched-chain amino acids were visible in the matrix. The test compositions were evaluated and the results of the organoleptic test scoring are also set forth in Table 10.

TABLE 10

| BRANCHED-CHAIN AMINO ACID FORTIFICATION | | | |
|---|---|---|---|
| | "high" test | "low" test | control |
| BCM in gm/237 mL serving | | | |
| valine | 2.5 | 1.3 | 0 |
| leucine | 2.5 | 1.3 | 0 |
| isoleucine | 2.5 | 1.3 | 0 |
| Total | 7.5 | 3.9 | 0 |

TABLE 10-continued

BRANCHED-CHAIN AMINO ACID FORTIFICATION

|  | "high" test | "low" test | control |
|---|---|---|---|
| TASTE TEST SCORE |  |  |  |
| bitter | 1.5 to 2 | 1.5 | none |
| sour | 0.5 | 0.5 | none |

Based on the results of this taste session, the evaluators collectively agreed that the bitter and sour flavor notes attributed to the branched-chain amino acids are less than ideal for a ready-to-use oral nutritional composition. Thus, in one embodiment of this invention, any additional branched-chain amino acids are supplied to patient in the form of a pill or capsule distinct from the liquid nutritional of the invention.

EXAMPLE III

The effect of nutritional intervention with $\omega$-3 fatty acids, branched-chain amino acids and antioxidants in the nutritional compositions of the invention, on prevention and treatment of cachexia can be monitored by any of the methods known to one skilled in the art, including but not limited to measuring: (i) food intake, body weight and anthropometric measurements; (ii) serum levels of lipids, fatty acids, amino acids and antioxidants; (iii) levels of serologic markers where appropriate, e.g., carcinoembryonic (CEA) antigens, serotonin, C-reactive protein, TNF and IL-1; (iv) changes in the morphology of tumors using techniques such as computed tomographic (CT) scan, ultrasonography, magnetic resonance imaging (MRI) and position emission tomography (PET).

Patients with hepatocellular carcinoma showing symptoms of cachexia are provided with the nutritional product of the invention with small, frequent feedings after surgical resection if the liver tumor is localized and small, or along with a regimen of chemotherapy. The liver functions and characteristics of the hepatic carcinomas are tested by procedures known in the art.

The daily nutritional management of liver cancer, therefore, includes administration of 2 to 4 containers of 8 ounce servings (237 mL) of the nutritional composition providing a daily amount of: (i) combined EPA and DHA in the range of 3 to 6 g, with the preferred dosage being about 3 g; (ii) branched-chain amino acids in the range of 5 to 25 g, with the preferred dosage being about 10–15 g branched-chain amino acids; and (iii) vitamin C in the range of 125 to 500 mg, with the preferred dosage being about 300 mg vitamin C; (iv) vitamin E in the range of 50 to 250 IU, with the preferred dosage being about 150 IU vitamin E; (v) beta-carotene in the range of 1250 to 3250 $\mu$g, with the preferred dosage being about 2500 beta-carotene $\mu$g; (vi) selenium in the range of 40 to 60 $\mu$g, with the preferred dosage being about 45 $\mu$g selenium. The effect of nutritional intervention on cancer cachexia and anorexia are monitored at monthly intervals (or as recommended in the clinical follow-up) as known in the art, and depending on the results obtained, the therapeutic regimen is developed to maintain and/or boost the weight gain by the patient, with the ultimate goal of achieving tumor regression and complete eradication of cancer cells.

For the underweight breast cancer patient on adjuvant chemotherapy, administration of the nutritional composition of the invention is started any time after surgery. The nutritional composition used in breast cancer patients is designed to maintain an adequate intake in spite of nausea, mucositis, and other side effects of chemotherapy. Patients receiving radiation therapy for breast cancer receive effective amounts of the nutritional composition to promote maintenance and repair of body tissue. The therapeutic and/or prophylactic regimens used in breast cancer patients are the same as those described in Section 6 above for patients recovering from hepatocellular carcinoma. The procedures of monitoring the patient under clinical evaluation for prevention and treatment of cachexia and anorexia in breast cancer are known in the art.

EXAMPLE IV

A pilot study was conducted to assess the effectiveness of a specific formula in ameliorating the cachexia of cancer patients. The formula of Example I was prepared. In addition to other nutrients, it contained (per two 237 mL servings) the long-chain $\omega$-3 fatty acids, the fructooligosaccharide ("FOS") and the antioxidant system specified in Table 10.

TABLE 10

TRIAL PRODUCT

| Ingredient | Amount per 2 × 237 mL servings |
|---|---|
| EPA $\omega$3 | 2.0 gm |
| DHA $\omega$-3 | 0.92 gm |
| fructooligosaccharide | 5.8 gm |
| beta carotene | 2.8 mg |
| vitamin G | 300. mg |
| vitamin E | 150. IU |
| selenium | 58. mcg |

In the pilot clinical trial of this example, ten patients with pancreatic cancer were evaluated. These patients were cachectic and losing weight at a mean rate of 0.86 kg per week over an average of 22 weeks (range: 11 to 56 weeks) prior to the trial. Over a three week trial period, patients consumed an average of two 237 mL (8 fluid ounces) servings per day as a supplement to their diets. After the trial period the group demonstrated a mean increase in weight of 2.1 kg (up from baseline), which translates to a mean weekly weight gain of 0.7 kg (See Table 11).

TABLE 11

Patients' Age, Gender and Weight Status

| Patient | Patient Age and Gender | Mean Weekly Wt (kg) Change up to Baseline | Baseline weight (kg) | Weight after three week trial (kg) | Mean Weekly Wt change during trial |
|---|---|---|---|---|---|
| 1 | 56f | −0.4 | 51 | 51.75 | 0.25 |
| 2 | 64m | −1.2 | 67 | na | na |
| 3 | 70m | −0.5 | 61 | 67.5 | 2.17 |
| 4 | 60m | −0.9 | 43 | 44 | 0.33 |
| 5 | 53f | −1.4 | 90 | 90.5 | 0.17 |
| 6 | 51f | −1.2 | 44.5 | 45.5 | 0.33 |
| 7 | 67m | −0.6 | 57 | 58 | 0.33 |
| 8 | 75f | −0.8 | 55 | 59 | 1.33 |
| 9 | 57m | −0.6 | 69 | na | na |
| 10 | 53f | −1 | 57.5 | na | na |
| Mean |  | −0.86 |  |  | 0.7 |

In addition, much of the weight gained was lean body mass. The group demonstrated a mean increase in lean body mass of 2.1% and a decrease in C-reactive protein ("CRP") levels (See Table 12). Serum CRP is a biochemical surrogate for the presence and progress of cancer cachexia, and shows a strong positive correlation. (Falconer, J. S. et al., *Cancer* 1995, 75:2077). Patients with serum CRP levels >10 mg/L are frankly cachectic. The mean CRP level at baseline was 31.5 and this dropped to about 10 after 3 weeks on the experimental formula of the invention. Thus, the invention improves cachexia in pancreatic cancer patients.

TABLE 12

Patients' Lean Body Mass and CRP

| Patient | % Lean Body Mass at Baseline | % Lean Body Mass after trial | Change in % Lean Body Mass | Baseline CRP mg/L | CRP after 3 week trial mg/L |
|---|---|---|---|---|---|
| 1 | 79.4 | 82.9 | 3.5 | 69 | <10 |
| 2 | 85.6 | na | na | 81 | na |
| 3 | 84 | 92.2 | 8.2 | 27 | <10 |
| 4 | 85.6 | 86.3 | 0.7 | <10 | <10 |
| 5 | 73.7 | 75 | 1.3 | <10 | <10 |
| 6 | 79.7 | 80.7 | 1 | 63 | <10 |
| 7 | 90.2 | 91.9 | 1.7 | <10 | 10 |
| 8 | 81.4 | 80.1 | −1.3 | <10 | <10 |
| 9 | 82.6 | na | na | 25 | na |
| 10 | 86.9 | na | na | <10 | na |
| Mean | 82.9 | 84.2 | 2.1 | 31.5 | 10* |

*CRP values read as <10 are assumed to be 10 for calculation of mean

The present invention is not to be limited to the scope by the specific embodiments described herein. Indeed, various modifications of the invention in addition to those described herein will become apparent to those skilled in the art from the foregoing description. Such modifications are intended to fall within the scope of the appended claims.

Various publications and patents are cited herein, the disclosures of which are incorporated by reference in their entireties.

We claim:

1. A liquid nutritional composition comprising:
   (a) at least 1000 mg per liter of ω-3 fatty acids, wherein the weight ratio of ω-6 fatty acids to ω-3 fatty acids is from about 0.1 to about 1.0;
   (b) at least 50 grams per liter of a source of amino-nitrogen, wherein 15 to 50% by weight of the amino-nitrogen is branched-chain amino acids, and wherein tryptophan is present in an amount less than about 5.0% by weight of the total amino-nitrogen, and;
   (c) at least 1 gram per liter of an antioxidant system comprising beta-carotene, vitamin C, vitamin E and selenium.

2. The composition according to claim 1 in which said ω-3 fatty acids are present in a quantity of about 1.0 gram to about 100 grams per liter.

3. The composition according to claim 1 in which said ω-3 fatty acids are present in a quantity of about 5.0 grams to about 100 grams per liter.

4. The composition according to claim 1 in which said ω-3 fatty acids are present in a quantity of about 5.0 grams to about 10.0 grams per liter.

5. The composition according to any one of claims 2–4 in which 15% to 25% by weight of the amino-nitrogen is branched-chain amino acids.

6. The composition claim 5 in which said tryptophan is present in an amount of less than 3.0% by weight a nitrogen.

7. A liquid nutritional composition comprising:
   a) at least 1000 mg per liter of ω-3 fatty acids, wherein the weight ratio of ω-6 fatty acids to ω-3 fatty acids is about 0.1 to about 1.0;
   (b) at least 50 grams per liter of a source of amino-nitrogen, wherein 15 to 50% by weight of the amino-nitrogen is branched-chain amino acids, and wherein tryptophan is present in an amount less than about 5.0% by weight of the total amino-nitrogen, and;
   c) an antioxidant component comprising about 2,500 to about 6,500 micrograms per liter of beta-carotene, about 250 to about 1,000 milligrams per liter of vitamin C, about 100 to about 500 I.U. per liter of vitamin E, and about 75 to about 125 micrograms per liter of selenium.

8. The composition according to claim 7 in which said ω-3 fatty acids are present in a quantity of about 1.0 gm to about 100 grams per liter.

9. The composition according to claim 7 in which said ω-3 fatty acids are present in a quantity of about 5.0 grams to about 100 grams per liter.

10. The composition according to claim 7 in which said ω-3 fatty acids are present in a quantity of about 5.0 grams to about 10.0 grams per liter.

11. The composition according to any one of claims 7–10 in which 15% to 25% by weight of the amino-nitrogen is branched-chain amino acids.

12. The composition according to claim 11 in which said tryptophan is present in an amount of less than 3.0% by weight of the total amino-nitrogen.

13. A liquid nutritional composition comprising:
   a) optionally at least 50 grams per liter of a source of amino-nitrogen, wherein 15 to 50% by weight of the amino-nitrogen is branched-chain amino acids, and wherein tryptophan is present in an amount less than about 5.0% by weight of the total amino-nitrogen;
   b) an antioxidant component comprising about 2,500 to about 6,500 micrograms per liter of beta-carotene, about 250 to about 1,000 milligrams per liter of vitamin C, about 100 to about 500 I.U. per liter of vitamin E, and about 75 to about 125 microgram per liter of selenium, and;
   c) an oil blend further comprising 5–40 wt. % canola oil, 10–50 wt. % medium chain triglyceride oil, 25–80 wt. % fish oil, 3–30 wt. % soybean oil, and 2–6 wt. % soy lecithin.

14. The liquid nutritional according to claim 13 in which said oil blend further comprises 9.3 wt. % canola oil, 16.2 wt. % medium chain triglyceride oil, 65 wt. % fish oil, 5.5 wt. % soybean oil, and 4.0 wt. % soy lecithin.

15. A liquid nutritional composition comprising:
   a) an antioxidant component comprising about 2,500 to about 6,500 micrograms per liter of beta-carotene, about 250 to about 1,000 milligrams per liter of vitamin C, about 100 to about 500 I.U. per liter of vitamin E, and about 75 to about 125 microgram per liter of selenium, and;
   b) at least 1000 mg per liter of ω-3 fatty acids, wherein the weight ratio of ω-6 fatty acids to ω-3 fatty acids is about 0.1 to about 1.0.

16. The composition according to claim 15 in which said ω-3 fatty acids are present in a quantity of about 1.0 gm to about 100 grams per liter.

17. The composition according to claim 15 in which said ω-3 fatty acids are present in a quantity of about 5.0 grams to about 100 grams per liter.

18. The composition according to claim 15 in which said ω-3 fatty acids are present in a quantity of about 5.0 grams to about 10.0 grams per liter.

19. A liquid nutritional composition comprising:
a) at least 50 grams per liter of a source of amino-nitrogen, wherein 15 to 50% by weight of the amino-nitrogen is branched-chain amino acids, and wherein tryptophan is present in an amount less than about 5.0% by weight of the total amino-nitrogen;
b) an antioxidant component comprising about 2,500 to about 6,500 micrograms per liter of beta-carotene, about 250 to about 1,000 milligrams per liter of vitamin C, about 100 to about 500 I.U. per liter of vitamin E, and about 75 to about 125 microgram per liter of selenium, and;
c) at least 4.47 grams of eicosapentaenoic acid per liter.

20. A liquid nutritional composition comprising:
a) an antioxidant component comprising about 2,500 to about 6,500 micrograms per liter of beta-carotene, about 250 to about 1,000 milligrams per liter of vitamin C, about 100 to about 500 I.U. per liter of vitamin E, and about 75 to about 125 microgram per liter of selenium, and;
b) at least 4.47 grams of eicosapentaenoic acid per liter.

* * * * *

UNITED STATES PATENT AND TRADEMARK OFFICE
CERTIFICATE OF CORRECTION

PATENT NO. : 6,077,828
DATED : June 20, 2000
INVENTOR(S) : Bonnie C. Abbruzzese, Mark A. McCamish, Frederick O. Cope, Stephen J. DeMichele It is certified that error appears in the above-identified patent and that said Letters Patent is hereby corrected as shown below:

Title page,
Inventors, the name of the last inventor is spelled correctly, but the "m" in DeMichele should be capitalized.

Claims,
Claim 6,
Should read: The composition in claim 5 in which said tryptophan is present in an amount of less than 3.0% by weight amino-nitrogen.

Signed and Sealed this

Second Day of October, 2001

Attest:

NICHOLAS P. GODICI
Attesting Officer    Acting Director of the United States Patent and Trademark Office